US006932774B2

(12) United States Patent
Nakatani et al.

(10) Patent No.: US 6,932,774 B2
(45) Date of Patent: Aug. 23, 2005

(54) RESPIRATORY MONITORING SYSTEM

(75) Inventors: Hiroto Nakatani, Nagoya (JP); Kenichi Yanai, Nisshin (JP); Noriyuki Ozaki, Kariya (JP)

(73) Assignee: Denso Corporation, Kariya (JP)

(*) Notice: Subject to any disclaimer, the term of this patent is extended or adjusted under 35 U.S.C. 154(b) by 91 days.

(21) Appl. No.: 10/606,968

(22) Filed: Jun. 27, 2003

(65) Prior Publication Data

US 2004/0010202 A1 Jan. 15, 2004

(30) Foreign Application Priority Data

Jun. 27, 2002 (JP) ....................................... 2002-187899
Jun. 27, 2002 (JP) ....................................... 2002-187904

(51) Int. Cl.⁷ ................................................ A61B 5/08
(52) U.S. Cl. ...................................................... 600/534
(58) Field of Search ................................ 600/529–543

(56) References Cited

U.S. PATENT DOCUMENTS

| | | | | | |
|---|---|---|---|---|---|
| 5,796,340 | A | * | 8/1998 | Miller | .................... 340/573.7 |
| 5,989,193 | A | * | 11/1999 | Sullivan | ....................... 600/534 |
| 6,280,392 | B1 | * | 8/2001 | Yoshimi et al. | .............. 600/534 |
| 6,375,621 | B1 | * | 4/2002 | Sullivan | ...................... 600/484 |
| 6,450,957 | B1 | | 9/2002 | Yoshimi et al. | |
| 6,547,743 | B2 | * | 4/2003 | Brydon | ........................ 600/534 |

FOREIGN PATENT DOCUMENTS

| | | |
|---|---|---|
| JP | A-6-225864 | 8/1994 |
| JP | A-8-131421 | 5/1996 |
| JP | A-8-215163 | 8/1996 |
| JP | A-2001-70256 | 3/2001 |

* cited by examiner

Primary Examiner—Robert L. Nasser
Assistant Examiner—Navin Natnithithadha
(74) Attorney, Agent, or Firm—Posz Law Group, PLC

(57) ABSTRACT

A microcomputer included in a respiratory monitoring system selects sensors that have output signals related to respiration of a person from sensors detecting forces applied by the person. To select the sensors, levels of the signals are compared between a respiratory frequency band and another frequency band. If the level of the signal in the respiratory frequency band is predetermined times higher than that of the signal in the other frequency band, the sensor is selected. The respiratory curve is produced based on weight signals outputted from the selected sensors.

21 Claims, 15 Drawing Sheets

RESPIRATORY MONITORING SYSTEM

CROSS REFERENCE TO RELATED APPLICATION

This application is based on and incorporates herein by reference Japanese Patent Applications No. 2002-187899 filed on Jun. 27, 2002 and No. 2002-187904 filed on Jun. 27, 2002.

FIELD OF THE INVENTION

The present invention relates to a respiratory monitoring system for monitoring respiratory conditions during sleep.

BACKGROUND OF THE INVENTION

A respiratory monitoring system for monitoring respiratory conditions of patients having respiratory disorders is disclosed in U.S. Pat. No. 6,450,957 (JP-A-2001-37742). This system includes weight sensors arranged under a sleeping pad in predetermined patterns. When weights are applied to the sensors, the sensors output signals corresponding to the applied weights.

A respiratory signal in a band of frequencies corresponding to a respiratory rate of a patient is produced based on the signals from the weight sensors. The system performs frequency analysis on the weight signals and calculates a power spectrum of the band. Then, it produces respiratory signals based on the weight signal outputted from the weight sensor having the strongest power spectrum.

However, weight variations caused by factors other than respiratory movement are also applied to the sensors. For example, weights vary due to weight or body movements of patients. As a result, the power spectrum of the band becomes stronger and an accuracy of the respiratory signal decreases.

SUMMARY OF THE INVENTION

The present invention therefore has an objective to provide a respiratory monitoring system that has an improved accuracy of respiratory signals. The respiratory monitoring system of the present invention includes weight sensors, a respiratory signal producing means, and a weight sensor selecting means.

The weight sensors, arranged in predetermined patterns, produce weight signals corresponding to weights applied to the sensors. The respiratory signal producing means produces respiratory signals corresponding to the respiratory condition of a person under respiratory monitoring during sleep.

The weight sensor selecting means selects the weight sensors that have outputs related to respiration of the person from the weight sensors sensing the weights. The sensor selecting means makes determination of the selection based on a comparison of the respiratory signals between a respiratory frequency band and another frequency band. The signal producing means produces the respiratory signals based on the weight signals outputted from the selected weight sensors.

The sensor selecting means selects the weight sensors that have outputs in the respiratory frequency band distinguishably larger than ones in other frequency bands. The signal producing means produces the respiratory signals based on the outputs of the selected sensors. In other words, the sensors under less influence of factors other than the respiration of the person are used for producing the respiratory signals. This improves an accuracy of the respiratory signals.

The respiratory monitoring system also detects apnea or hypopnea based on a variation in frequency of the respiratory signal.

BRIEF DESCRIPTION OF THE DRAWINGS

The above and other objectives, features and advantages of the present invention will become more apparent from the following detailed description made with reference to the accompanying drawings. In the drawings.

DETAILED DESCRIPTION OF THE PREFERRED EMBODIMENT

Figure 1:
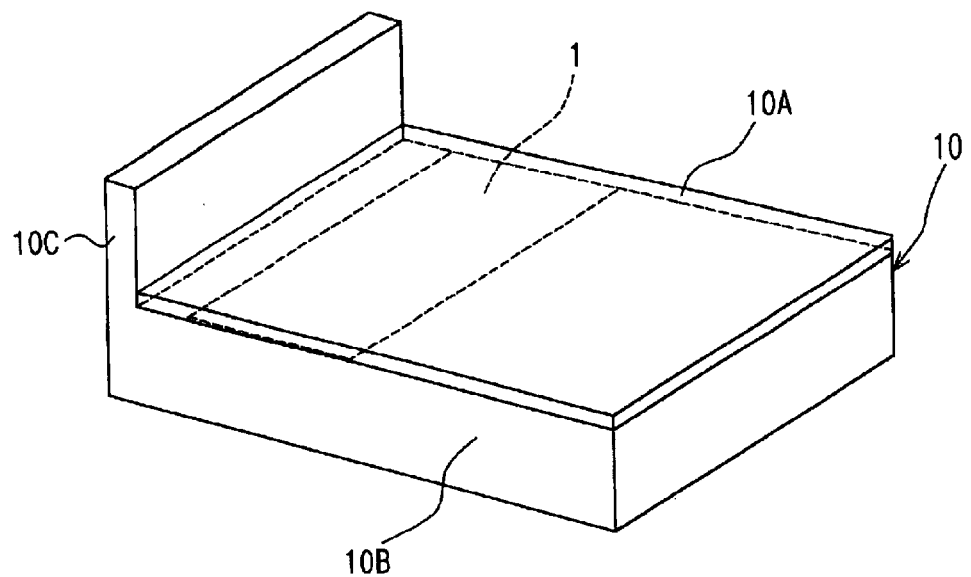
FIG. 1 a schematic view of a respiratory monitor system installed on a bed according to a first embodiment of the present invention.

The preferred embodiments of the present invention will be explained with reference to the accompanying drawings. In the drawings, the same numerals are used for the same components and devices.

[First Embodiment]

Referring to FIG. 1, a respiratory monitoring device 1 is inserted under a bed pad 10A that is placed on a bed 10. The bed 10 is constructed of a frame 10B and a headboard 12. The device 1 is positioned between the longitudinal center of the bed 10 and the head board 10C so that it corresponds to the torso of the person.

Figure 2:
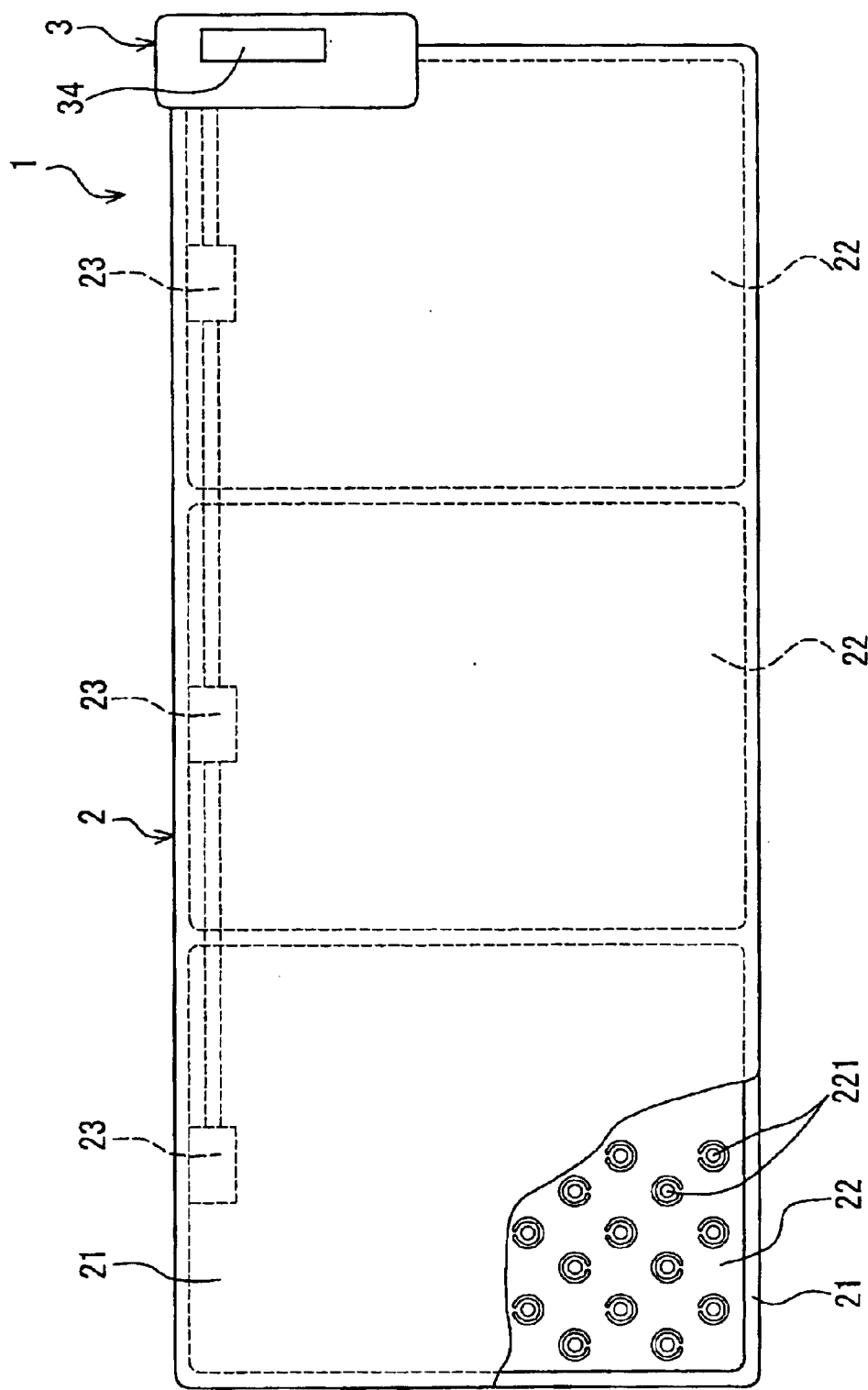
FIG. 2 is a schematic view of the respiratory monitoring system.

The device 1 includes a sheet pad 2 and a control unit 3 as shown in FIG. 2. The sheet pad 2 has three sensor sheets 22 sealed between sealing sheets 21. Each sensor sheet 22 has a sensor selecting unit 23 and one hundred and sixty two pressure-sensitive elements 221 arranged at substantially equal intervals. The elements 221 and the sensor selecting unit 23 are electrically connected via electrical wires or conductor traces (not shown).

The resistance of the elements 221 varies according to weights (forces) applied to the elements 221 when a voltage is applied to the system. As a result, the level of the voltage drop varies based on the variation in resistance. The weights applied to the elements 221 are independently determined based on the variation in the voltage drop level. In other words, the elements 221 can be used as weight sensors.

Figure 3:
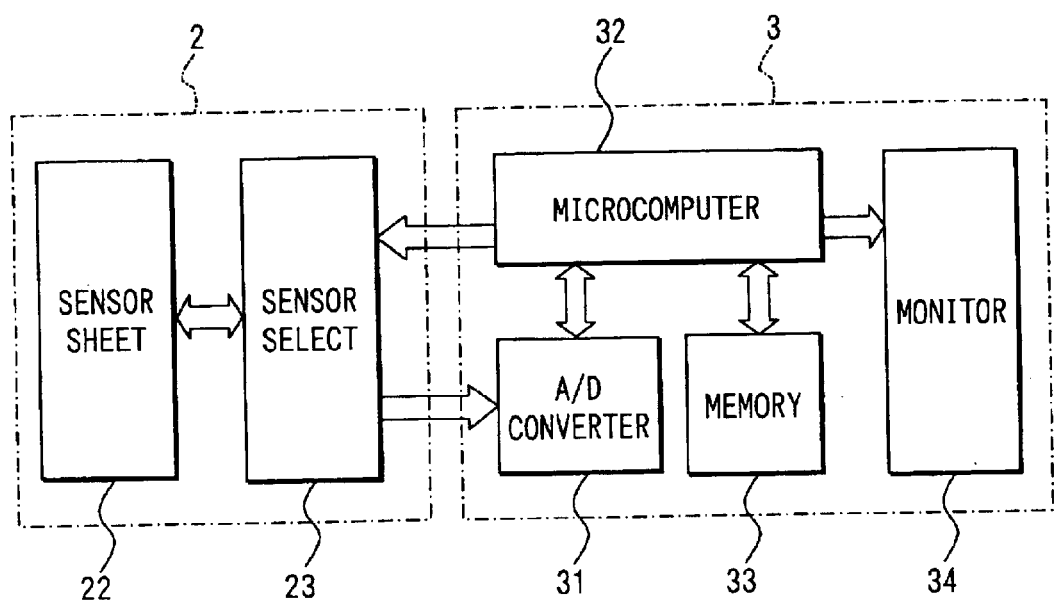
FIG. 3 is a block diagram of the respiratory monitoring system.

The control unit 3 includes an A/D converter 31, microcomputer 32, a memory 33, and a monitor 34 as shown in FIG. 3. The control unit 3 receives and selects weight signals from elements 221. Then, it converts the weight signals from analog to digital via the A/D converter 31, and stores the digital values in the microcomputer 32. At that time, the microcomputer 32 sends switching signals to the sensor selecting unit 23 to select the element 221 from which the microcomputer 32 receives the weight signal.

The microcomputer 32 outputs a respiratory curve that represents respiratory signals to the monitor 34. The monitor 34 is capable of numerically or graphically displaying respiratory conditions, such as a breathing intensity, or generating beep tones. With this configuration, the respiratory conditions of the person can be monitored without mounting sensors on the person.

Figure 4:
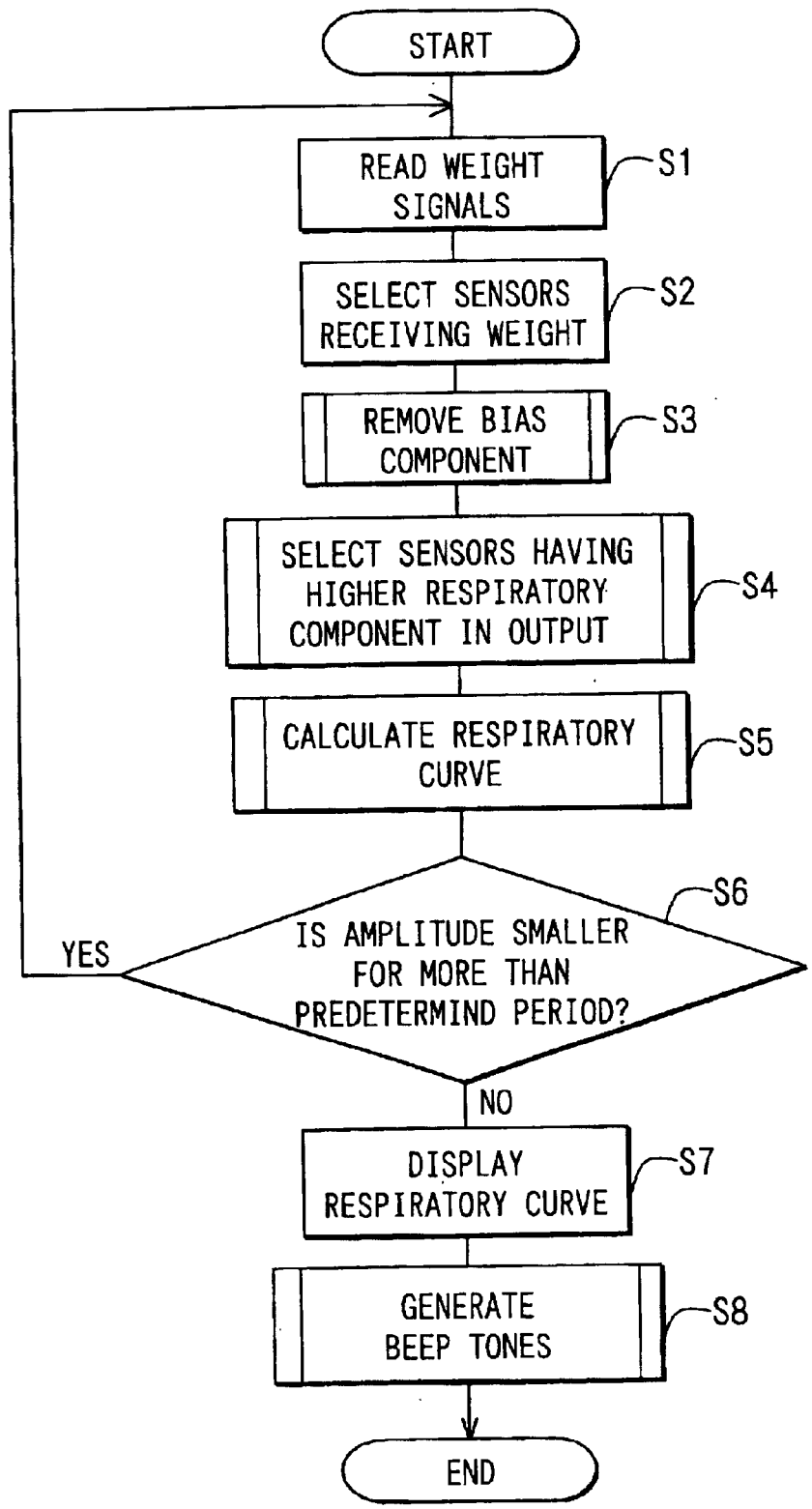
FIG. 4 is a flowchart showing a respiratory monitoring process performed by a microcomputer included in the respiratory monitoring system.

A respiratory monitoring process performed by the microcomputer 32 is shown in FIG. 4. The microcomputer 32 starts reading the weight signals in sequence from the elements 221 when the control unit 3 is turned on (S1). It selects the elements 221 that have output signals higher than a predetermined level (S2). In other words, voltage drops in the elements are less than a predetermined level. The selected elements 221 are determined that they receive the weight of the person.

The weight signals include bias components other than the variable components that vary according to the respiratory condition of the person. The bias components result from the weight of the person that applied to the sensors 221. The bias components of the elements 221 are removed (S3) to improve accuracy in determination of the respiratory condition.

Figure 5:
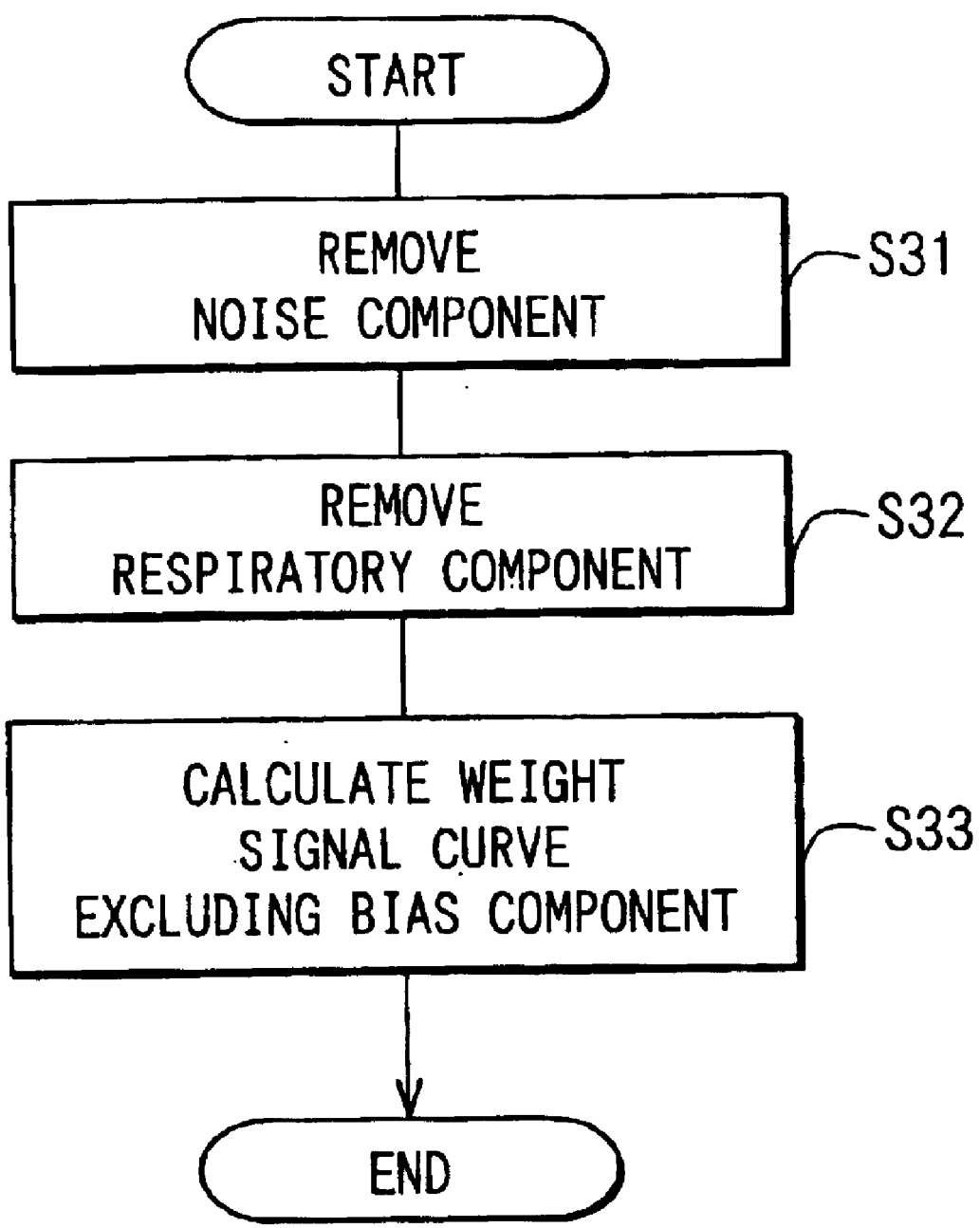
FIG. 5 is a flowchart showing a filtering process for removing a bias component from weight signals.
Figure 6A:
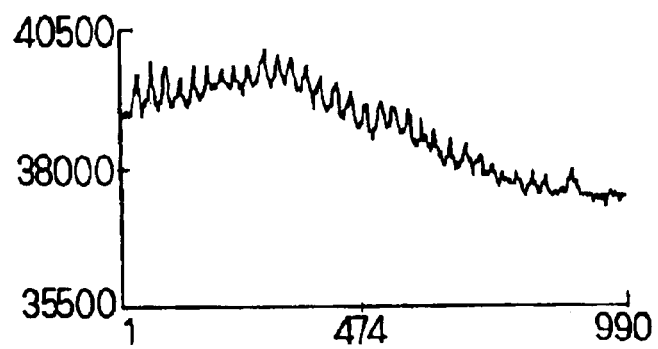
FIG. 6A is a waveform of a signal outputted from a weight sensor.
Figure 6B:
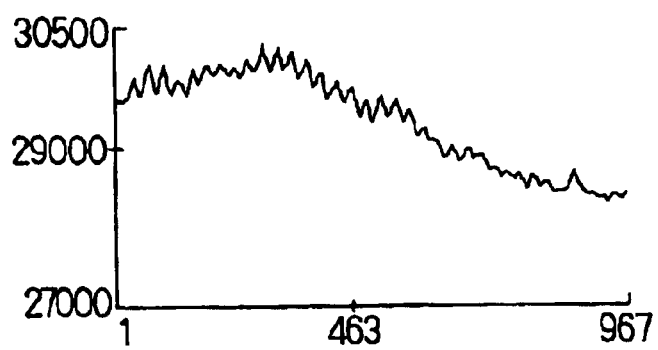
FIG. 6B is a waveform of the signal after the noise removal.

The bias components are removed by a digital noise filter. The filtering process, which corresponds to a bias component removing means, is shown in FIG. 5. A noise component of the signal higher than the frequency (0.2–0.5 Hz) corresponding to the respiratory rate is removed (S31). The digital noise filter used in this embodiment has a capability of removing noises higher than 3 Hz. An example of a raw signal outputted from the sensor 221 is shown in FIG. 6A. The result of filtering the signal shown in FIG. 6A by the noise filter is shown in FIG. 6B.

Figure 6C:
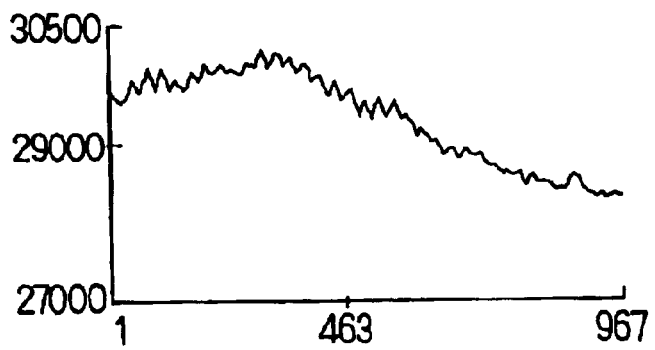
FIG. 6C is a waveform of the signal after a removal of a respiratory component that substantially corresponding to a respiratory rate of the person.

A digital respiratory component filter removes respiratory components substantially corresponding to the respiratory rate (S32). The digital filter used in this step has a capability of removing noises higher than 3 Hz. The result of filtering the signal shown in FIG. 6B by the respiratory component filter is shown in FIG. 6C.

Figure 6D:
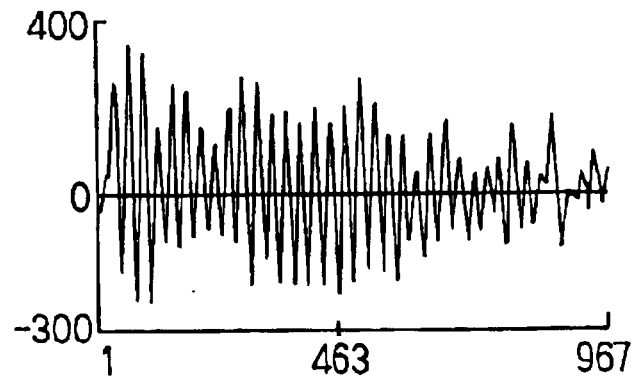
FIG. 6D is a waveform of the signal including only the respiratory component.

A weight signal curve that does not include bias components is calculated by subtracting the result obtained in step S32 from the result obtained in step S31 (S33). The weight signal curve is shown in FIG. 6D. Although a band-pass filter can be used for removing the bias components, the two-step filtering by the digital filter requires less filter orders and calculation time. The digital filters are not limited to the ones that filter signals higher than 3 Hz and 0.3 Hz, respectively.

Figure 7:
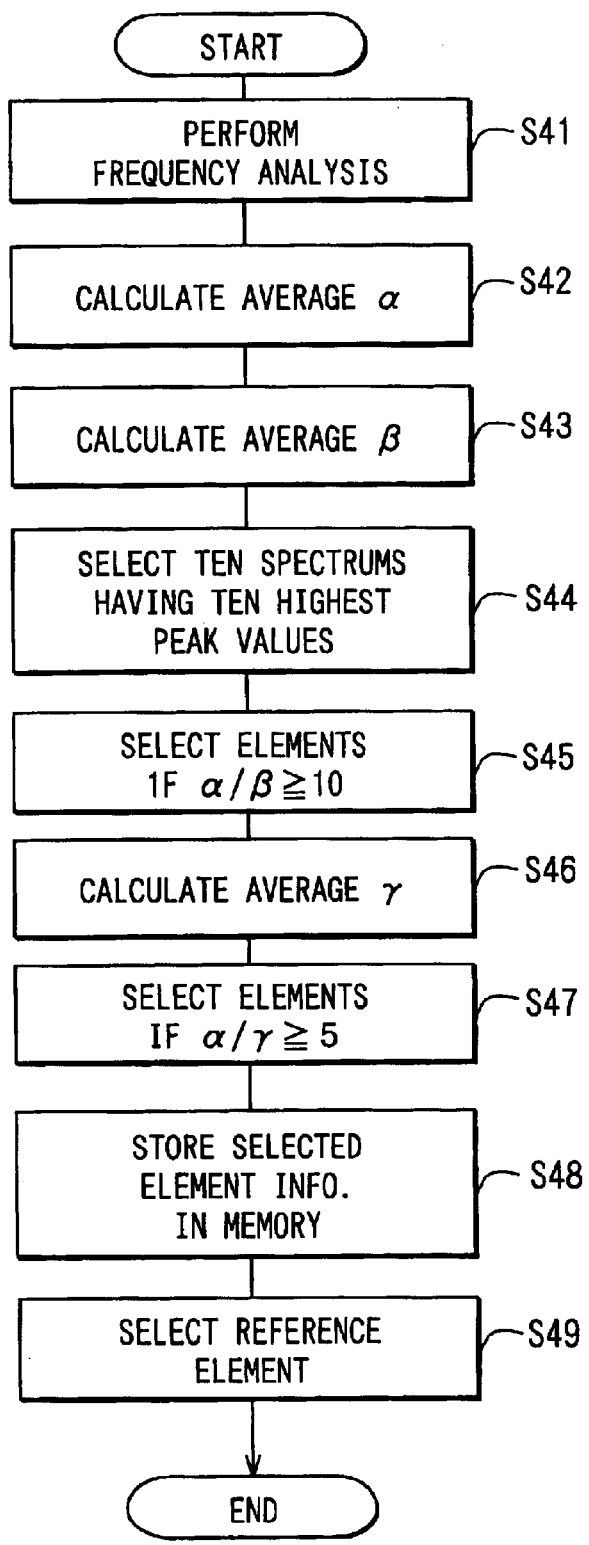
FIG. 7 is a flowchart showing a sensor selecting process.

The elements 221 that have output signals including higher levels of the respiratory components are selected (S4). Signals outputted from the selected sensors 221 are used for producing a respiratory signal. This improves the accuracy of the respiratory condition determination. A sensor selecting process is shown in FIG. 7. This process and the sensor selecting step S2 correspond to the weight sensor selecting means.

Figure 8A:
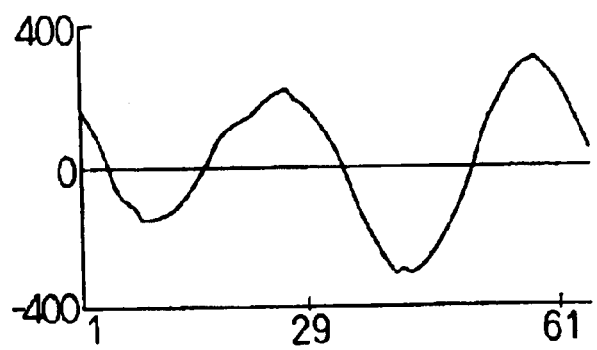
FIG. 8A is a waveform of a weight signal after the noise removal.
Figure 8B:
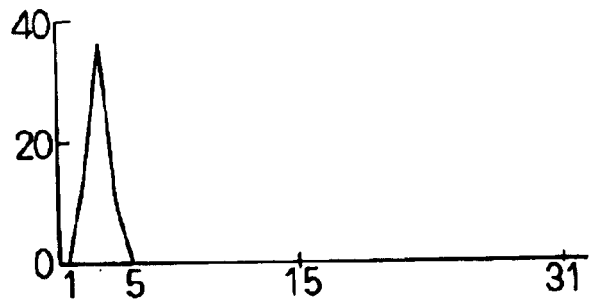
FIG. 8B is a power spectrum of the weight signal shown in FIG. 8A.

Frequency analysis is performed on the weight signal, the bias component of which is removed (S41). The frequency analysis is performed on all signals outputted from the elements selected in step S2. The weight signal, the bias component of which is removed, is shown in FIG. 8A. A power spectrum obtained after the step S41 is performed is shown in FIG. 8B.

An average α of power spectrum values in a respiratory frequency band is calculated (S42). An average β of power spectrum values higher than the respiratory frequency band (higher than 0.5 Hz) is calculated (S43). Ten power spectrums having ten highest peak values are selected (S44). The average α is compared with the average β to select the spectrums, the average α of which is at least ten times larger than the average β. The outputs of the elements 221 that correspond to the selected spectrums are used for producing the respiratory signals (S45).

Figure 8C:
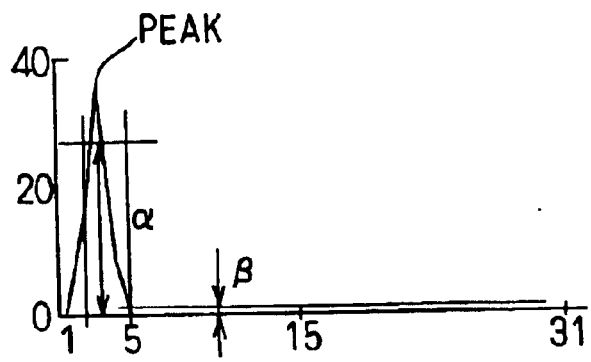
FIG. 8C is the power spectrum with a peak value, average values indicated.

In steps S44 and S45, correlation between the average α and the average β, and a peak value are calculated as shown in FIG. 8C. Then, the elements 221 are selected based on the calculation. An average γ of the power spectrums in a band lower than the respiratory frequency band (0.2 Hz) is calculated for each power spectrum selected in step S45 (S46). The average γ is compared with the average α and the spectrums, the average α of which is five times larger than the average γ, are selected. The outputs of the elements 221 that correspond to the selected spectrums are used for producing the respiratory signals (S47).

Figure 8D:
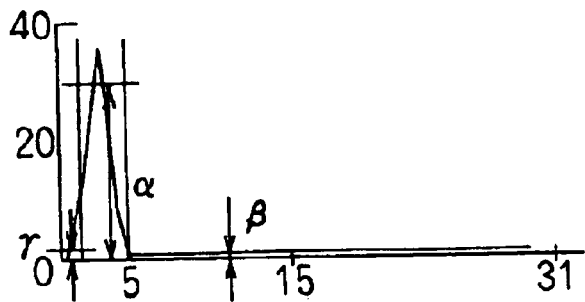
FIG. 8D is the power spectrum with average values indicated.

As shown in FIG. 8D, a correlation between the average α and the average γ is calculated and the elements 221 are further selected based on the calculation. Element numbers and weight signals of the elements 221 selected in step S47 are stored in the memory 33 (S48). The sensor 221 having the largest peak value of the power spectrum is selected from the selected elements 221 as a reference sensor for respiratory curve calculation (S49).

Figure 9:
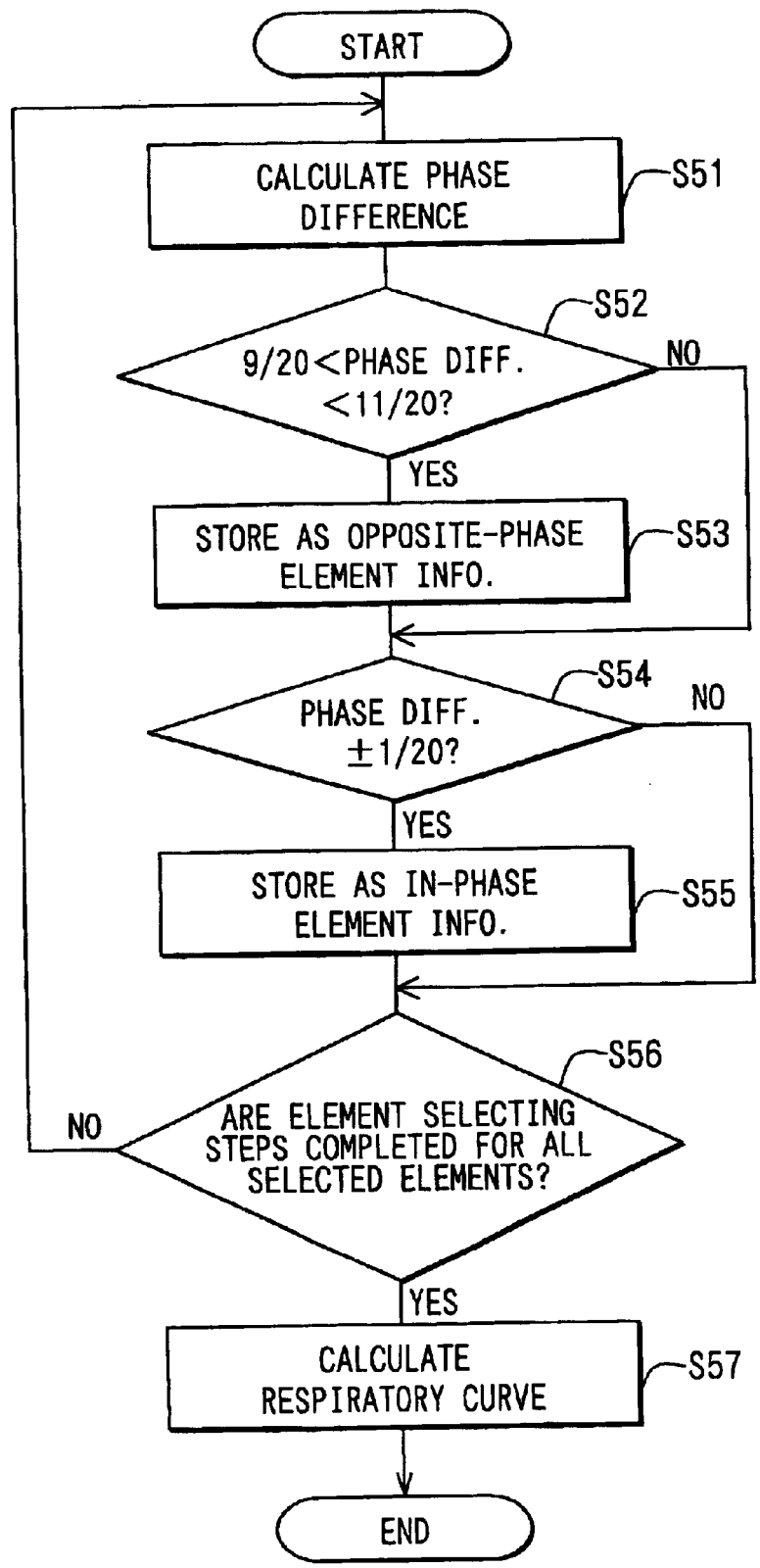
FIG. 9 is a flowchart showing a respiratory curve calculating process.

When the sensor selecting step (S4) is completed, the respiratory curve that represents the respiratory signals is calculated (S5). The respiratory curve calculation process is shown in FIG. 9. A phase difference between a signal of each selected element 221 and a signal of the reference sensor 221 is calculated (S51). The phase difference is calculated based on a correlation between signals of the selected elements 221 and the reference sensor 221, which is calculated after the bias component is removed.

It is determined whether the calculated phase difference is in opposite phase to the reference signal (S52). More specifically, it is determined whether the phase difference is within a range of 9/20 to 11/20 periods ($\pi\pm\pi/10$). If the phase difference is in opposite phase, information on the sensor 221 is stored in the memory 33 (S53). If the phase difference is not in opposite phase, it is determined whether the weight signal is substantially in phase with the reference element signal (S54). More specifically, it is determined whether the phase difference is in a rage of $\pm 1/20$ period ($0\pm\pi/10$). If the phase difference is in the range, information on the element 221 is stored as an element that produces an in-phase signal (S55).

It is determined whether the element selecting steps based on the phase difference is performed for all elements 221 selected in step S4 (S56). If the element selection is completed, the respiration curve calculation is performed (S57). The AD values of the opposite-phase weight signals, which are obtained after the bias components are removed, are multiplied by −1, respectively. The multiplied values are summed. The AD values of the in-phase weight signals, which are obtained after the bias components are removed, are summed. The sum of the results of the above calculations is divided by the number of the elements. This represents the respiratory curve. The respiratory curve calculating process corresponds to the respiratory signal producing means.

When step S5 is completed, it is determined whether an amplitude of the respiratory curve is smaller than a predetermined level for more than a predetermined period (S6). If the result of step S6 is yes, the steps are repeated from step 1 and the respiratory curve is recalculated using newly outputted weight signals. If the result of step S6 is no, the respiratory curve is displayed on the monitor 34 (S7).

Figure 10:
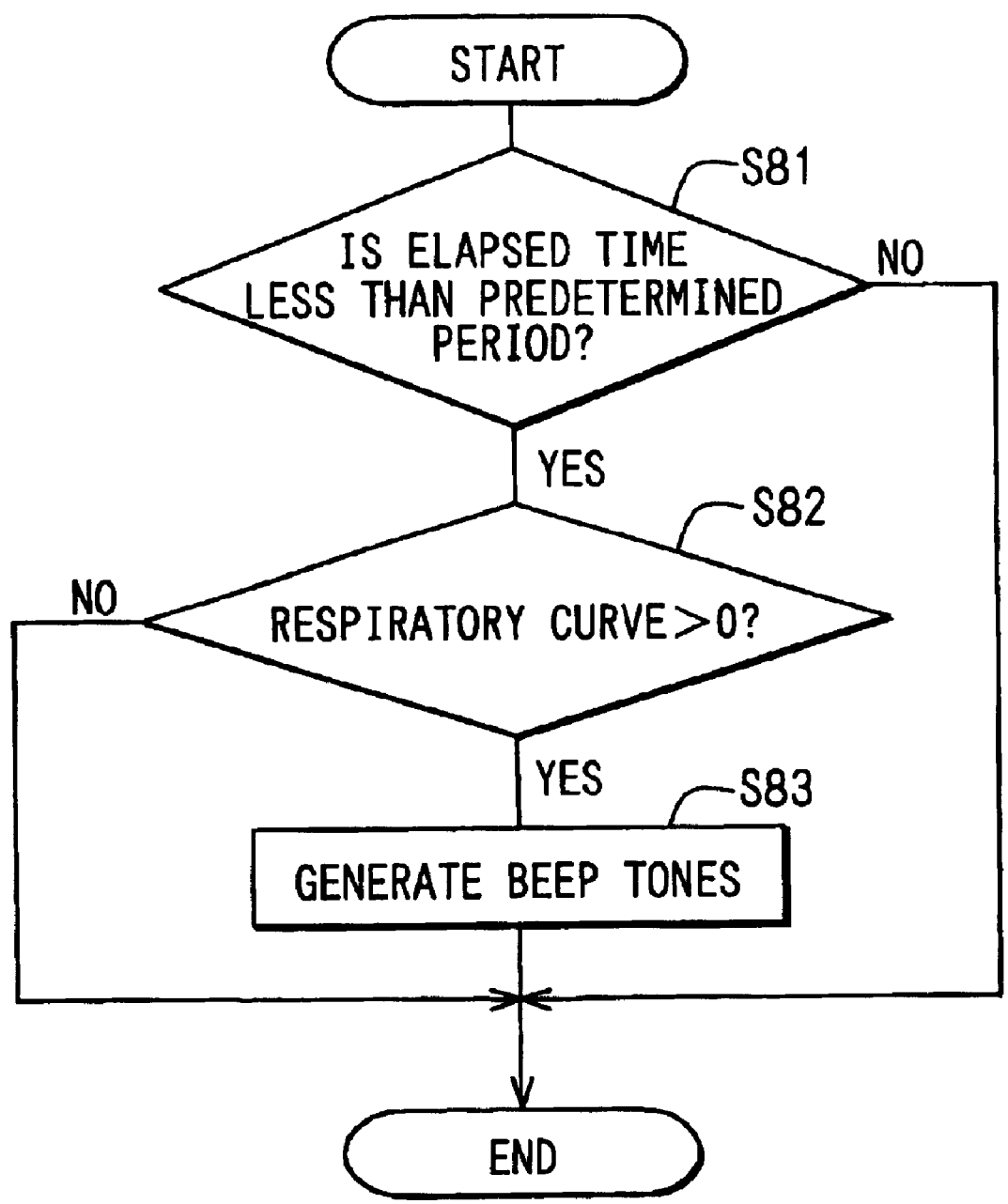
FIG. 10 is a flowchart showing a beep tone generating process.

When the respiratory curve is displayed, beep tones are generated in synchronization with the respiratory curve (S8). The beep tones indicate that the respiratory monitoring system A are not properly used. For instance, bed setting is improper or the system 1 is not properly positioned. The process for generating the beep tones is shown in FIG. 10.

First, it is determined whether an elapsed time since the proper production of the signals has started is less than the predetermined period (S81). If the time is more than the predetermined period, the process ends. This is because the person on the bed may be already asleep when the time is more than the predetermined period. Therefore, the beep tones are not generated so that they do not disturb the person.

If the time is less than the predetermined period, it is determined whether the respiratory curve is positive or negative (S82). If it is positive, the beep tones are generated (S83). In this case, the beep tones are generated in synchronized with the respiratory curve.

With the above configuration, elements 221, the signals of which in respiratory frequency are relatively larger than other signals can be selected. Then, the respiratory signals (respiratory curve) are generated based on the signals outputted from the selected elements 221. Furthermore, the bias components are removed from the weight signals. That is, the respiratory signals are produced based on the weight signals, the bias components of which are filtered.

When the weight signals do not include significant respiratory components, the respiratory signals are regenerated based on newly outputted weight signals. The beep tones are generated when the system 1 is not properly used. This improves an accuracy of the respiratory signals. Therefore, reliable respiratory signals are obtained. Only elements 221 to which the weight of the person is applied are selected before starting the signal processing. As a result, the process speed improves.

[Second Embodiment]

Figure 11:
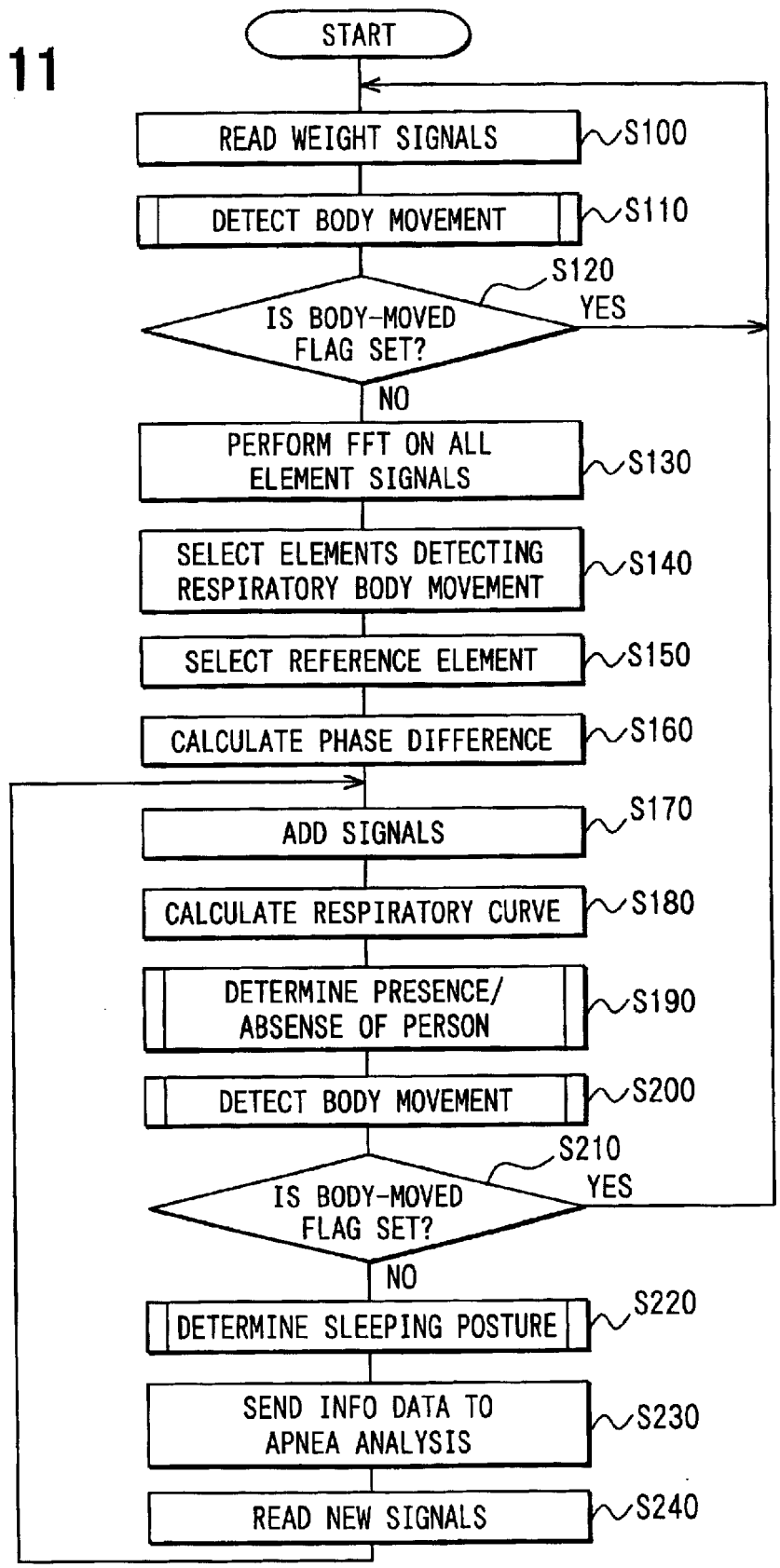
FIG. 11 is a flowchart showing a respiratory monitoring process performed by the microcomputer according to a second embodiment of the present invention.
Figure 12:
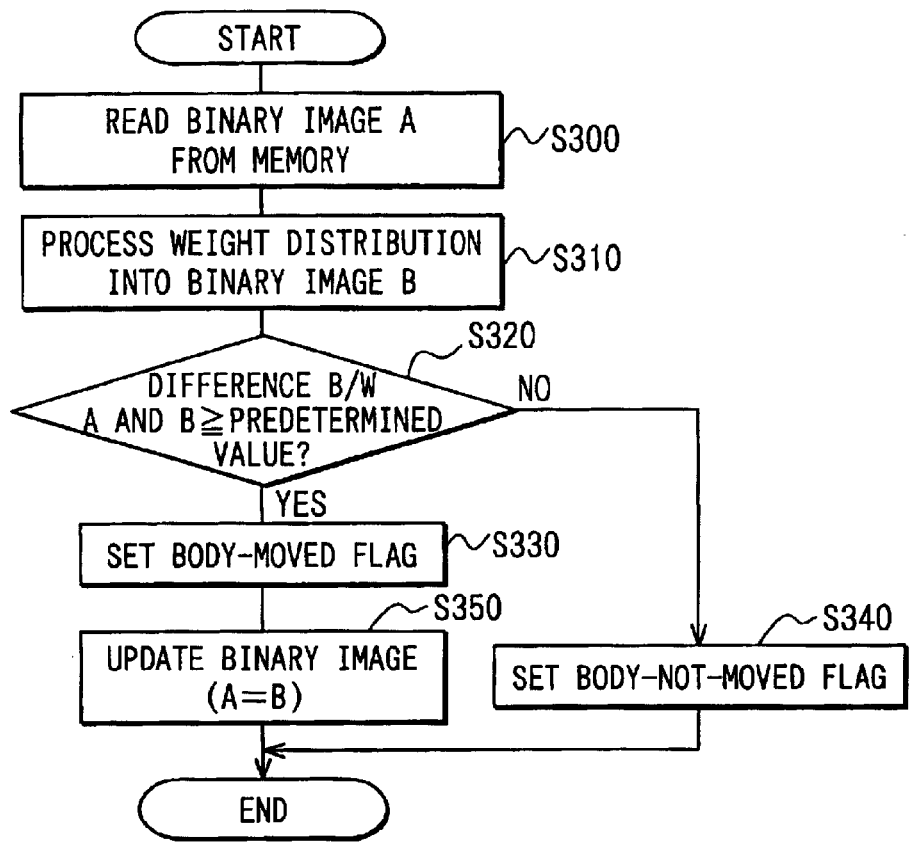
FIG. 12 is a flowchart showing a body movement detecting process.

Referring to FIG. 11, weight signals produced from pressure-sensitive elements 221 while a person sleeps on the bed are stored in the memory 33. A respiratory curve corresponding to body movements of the person due to respiration is calculated. The respiratory curve can be produced in synchronization with element signal detection.

Signals from the elements 221 are read into the microcomputer 32 (S100). It is determined whether the body movements occur and the sleeping posture of the person changes based on the read signals (S110). This determination is performed for reducing influences of the body movements that result in posture change to produce an accurate respiratory curve. Then, it is determined whether a body-moved flag that indicates an occurrence of the body movements is set (S120). When the posture change is detected, newly outputted element signals are read from the memory 33.

When the posture changing movement is not detected, the Fast Fourier Transform (FFT) is performed on all element signals for frequency analysis (S130). The elements 221 that indicate weight variations due to the respiratory body movement are selected based on sizes of power spectrums in a respiratory frequency range of 0.2–0.5 Hz (S140). The element 221, the power spectrum level of which is the highest, is selected as a reference element 221 for phase difference calculation (S150). The highest power spectrum represents the largest change in weight due to respiratory body movement.

A phase difference between a signal from each selected element 221 and a signal from the reference element 221 is calculated (S160). If the phase difference is between $-1/4\pi$ and $1/4\pi$, the signal is determined as an in-phase signal with respect to the reference signal. If the phase difference is between $3/4\pi$ and $-3/4\pi$ the signal is determined as an opposite-phase signal with respect to the reference signal. The signals having other phases with respect to the reference signal are not used for the respiratory curve calculation.

The in-phase signals are added to the reference signal and the opposite-phase signals are inverted and added (S170). The respiratory curve is produced by adding the reference signal, the in-phase signals, and the opposite-phase signals (S180). Presence/absence of the person on the bed is determined so that the respiratory monitoring is performed only when the person is present on the bed (S190). This improves an accuracy of the determination. When the person is absent, the respiratory curve is deleted from data for apnea analysis.

When the person presence/absence determination is completed, the body movement determination is performed again (S200). Then, it is determined whether the body-moved flag is set (S210). If the flag is set, the process is returned to step S100 for reading newly outputted signals and steps S100 to S180 are repeated. In other words, the signals are not used to produce the respiratory curve for the apnea/hypopnea determination as long as the body movement is detected. Thus, the respiratory curve that represents the respiratory body movements is produced without influence of the body movements that result in posture change.

If the flag is not set, the sleeping posture of the person is determined (S220). The posture is useful information for the apnea/hypopnea determination since the posture affects occurrences of the apnea and the hypopnea. Information on the respiratory curve is sent to the apnea analysis (S230). In this analysis, apnea or hypopnea is detected based on the respiratory curve. Newly outputted signals are read in the next step (S240). Since the same element is used as a reference element and the reference element determination is not performed as long as the posture changing body movement does not occur, the process returns to step S160.

Pressure distribution of the elements 221 is binarized on the basis of the weights detected by the elements whether they are higher than a predetermined value. The binarized weight distribution is processed into a binary image A and the binary image A is stored in the memory 33. The binary image A shows weight distribution of the pressure applied to the bed 10 by the person. The binary image A is read from the memory 33 for the body movement detection (S300).

The latest element signals from the elements 221 are compared with a predetermined value, and weight distribution is processed into a binary image B (S310). The binary image B is compared with the binary image A to determine whether a variation in weight distribution is present (S320). If the difference between the current number and the previous number of the elements 221 detecting the weights is more than a predetermined value, it is determined that the binary image B distinguishably differs from the binary image A. Then, the body-moved flag is set (S330). If the difference between the current number and the previous number is less than the predetermined value, the body-not-moved flag is set (S340).

If locations of the elements 221 detecting the weights differ by more than a predetermined number of the elements 221, it is determined the same as step S330. If it is determined that the binary image B distinguishably differs from the binary image A, the binary image A is updated to the binary image B and stored in the memory 33 (S350).

Figure 13:
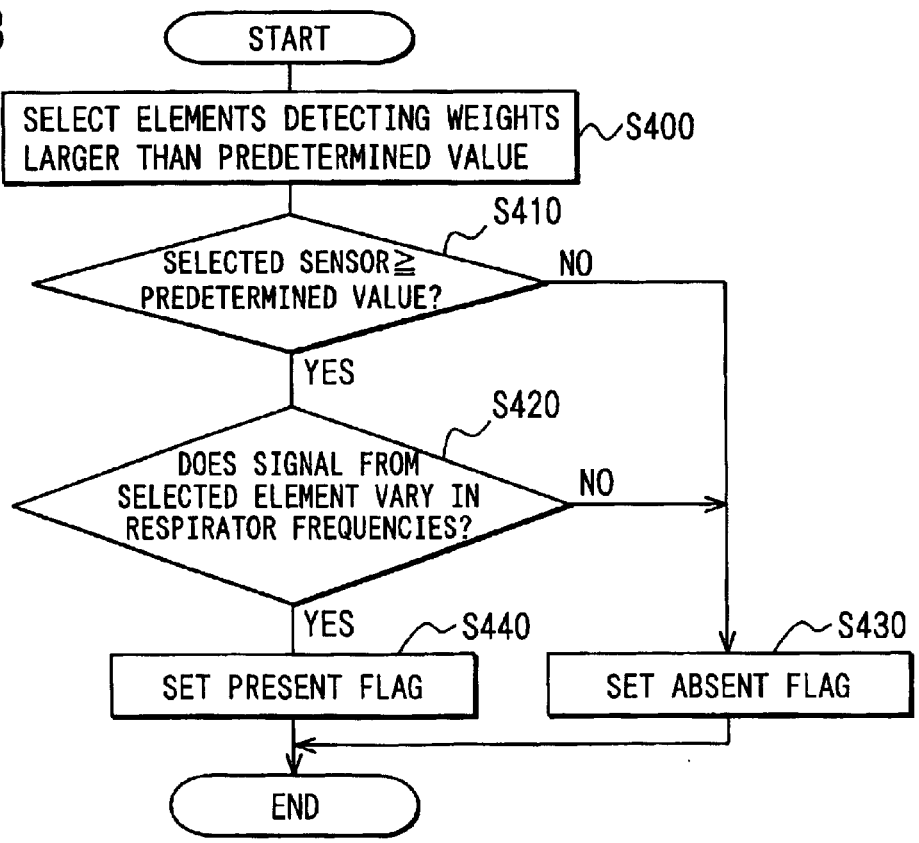
FIG. 13 is a flowchart showing a person presence detecting process.

The person presence detection process is shown in FIG. 13. The elements 221 detecting weights larger than a predetermined value are selected (S400). It is determined that the number of the elements 221 is more than the predetermined value (S410). If the number is lower than the predetermined value, it is determined that the person is not on the bed. The number of the elements 221 detecting the weights represents the area of the bed, in which the weight of the person is applied. Therefore, it is considered that the weight is not applied to the bed if the number is low.

It is determined whether the signals from the selected elements 221 vary in the respiratory frequencies to confirm that the presence of the person on the bed (S420). This is because the weight applied to the bed 10 may not be by the person but by an object put on the bed 10. If the signals vary in the respiratory frequencies, it explains that the person is present on the bed 10. A present flag that indicates the presence of the person on the bed is set (S440). If the signals do not vary in the respiratory frequencies, an absent flag that indicates the absence of the person is set (S430).

Figure 14:
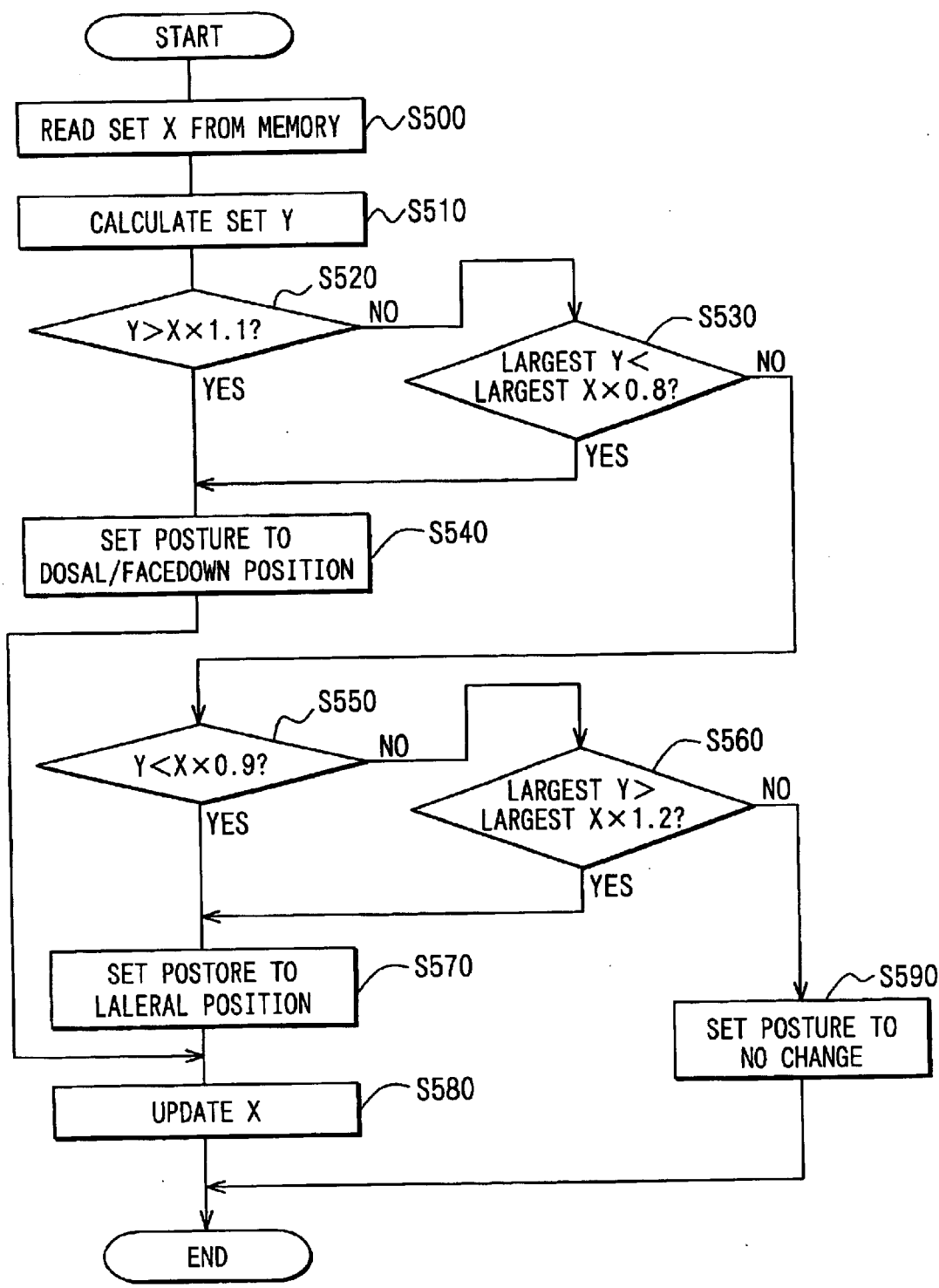
FIG. 14 is a flowchart showing a sleeping posture determining process.

The sleeping posture determination process is shown in FIG. 14. A default of the posture is set to a dorsal or a facedown position. A set x of the elements 221 detecting the weight of the person is read from the memory 33 (S500). The set x includes the number of the elements 221 and the applied weights. The information included in the set x is updated whenever a change in the posture is detected and the new information is stored in the memory 33.

The elements 221 detecting the weight are selected based on the element signals to calculate a set y of the elements (S510). It is determined whether the total number of the elements 221 in the set x is multiplied by 1.1. The total number of the elements 221 in the current set y is compared with the multiplied value (S520). If the total number in the set y is larger than the multiplied value, the posture is set to the dorsal position or the facedown position changed from the lateral position (S540).

If the total number is smaller than the multiplied value, the largest signal is selected from each set x, y, that is, the largest values of sets x, y are selected. The largest value of the set x is multiplied by 0.8 and compared with the largest value of the set y (S530). If the largest value of the set y is smaller than the multiplied value, the posture is set to the dorsal position or the facedown position changed from the lateral position (S540).

If the largest value of the set y is larger than the multiplied value, the total number of the elements in the set x is multiplied by 0.9. The total number of the elements in the set y is compared with the multiplied value (S550). If the total number is smaller than the multiplied value, the posture is set to the lateral position changed from the dorsal or the facedown position (S570).

If the total number is larger than the multiplied value, the largest value of the set x is multiplied by 1.2 and compared with the largest value of the set y (S560). If the largest value of the set y is larger than the multiplied value, the posture is set to the lateral position changed from the dorsal or the facedown position (S570).

If the largest value of the set y is smaller than the multiplied value, no change in the posture is determined (S590). If the change in the posture is determined in step S540 or S570, the information in the set x is updated with the information in the set y (S580).

Figure 15:
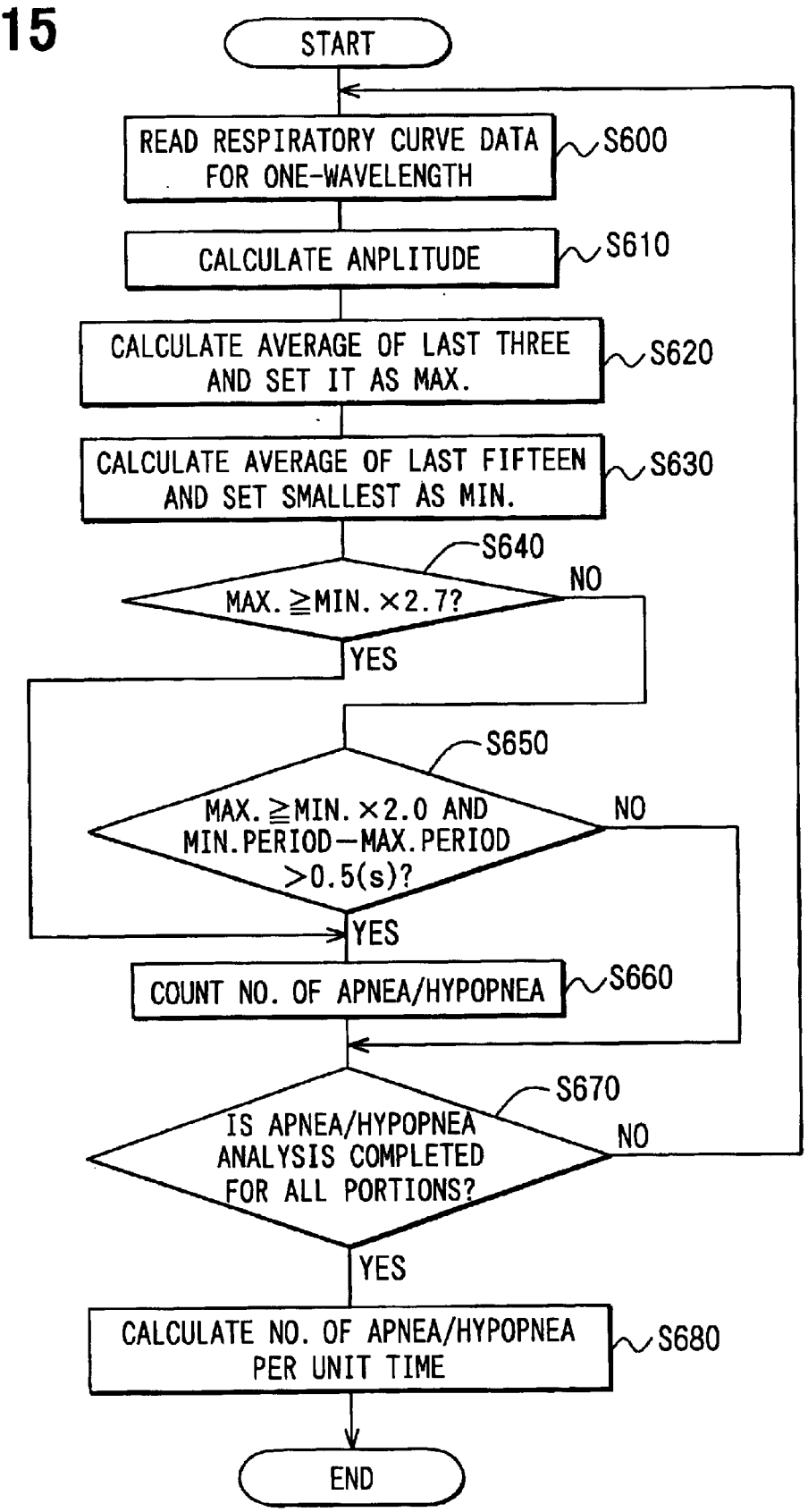
FIG. 15 is a flowchart showing an apnea analysis process.
Figure 16:
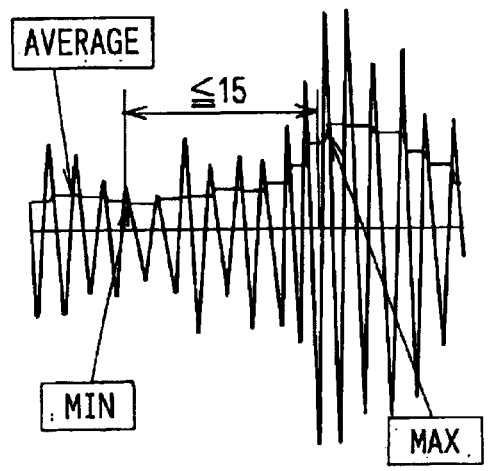
FIG. 16 is an explanatory diagram for maximum and minimum value settings.

The apnea analysis process is shown in FIG. 15. The respiratory curve is divided into one-wavelength portions and data on each portion is read (S600) and an amplitude of the portion is calculated (S610). An average of amplitudes of the last three portions from the newest data is calculated and set this average as the maximum value (S620). The minimum value is determined by selecting the smallest average from the average amplitudes of the last fifteen wavelengths (S630). One example of setting the maximum value and the minimum value is shown in FIG. 16.

The minimum value is multiplied by 2.7 and compared with the maximum (S640). If the maximum value is larger than the multiplied value, the occurrence of the apnea or hypopnea immediately before the maximum value is determined. Then, a counter for counting the occurrence of the apnea/hypopnea is incremented by 1 (S660).

If the maximum value is smaller than the multiplied value, the minimum value is multiplied by 2 and compared with the maximum value (S650). It is determined whether the maximum value is larger than the multiplied value and the period of the respiratory curve at the minimum value is longer than the period at the maximum value plus 0.5 second. If the result of the determination is yes, it is determined that the frequency of the respiratory curve changes from low to high, that is, the apnea or the hypopnea has occurred. If the result of the determination is no, it is determined whether apnea/hypopnea analysis is completed for all portions of the respiratory curve (S670). If it is not completed, the steps are repeated from step 600.

Figure 19:
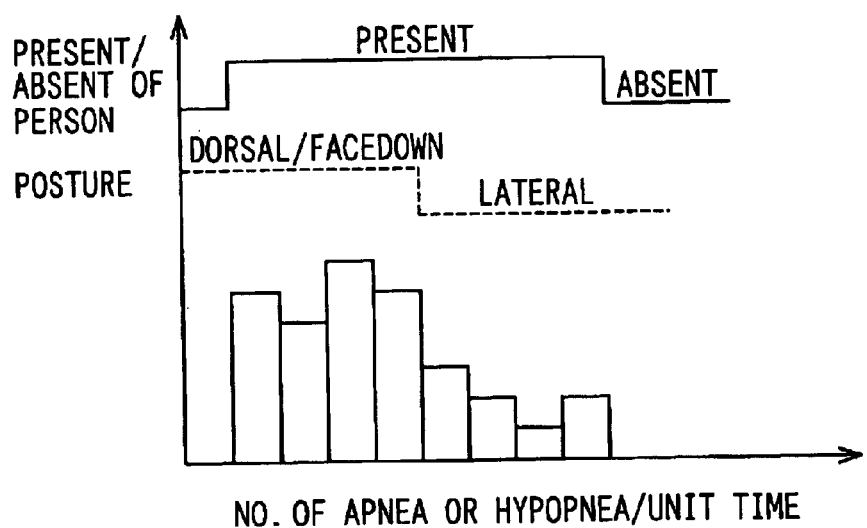
FIG. 19 is a schematic view of a display on a monitor.

The number of the apnea/hypopnea occurred in unit time is calculated based on the count obtained in step S660 (S680). The number is displayed on the monitor 34 along with the results of the person determination and the posture determination, and the respiratory curve. An example of the display on the monitor 34 is shown in FIG. 19 although the respiratory curve is not shown. The number of the apnea/hypopnea is confirmed by posture. Other information, including the total number of the apnea/hypopnea and an average of the apnea/hypopnea per unit time, may be displayed as well.

It is difficult to distinguish between the apnea and the hypopnea. In general, the respiratory body movement for recovering respiration after the apnea is larger than after the hypopnea. Thus, a main objective of the determination made in step 640 is for detecting the apnea. The hypopnea may not be accurately detected based on the variation in amplitudes of the respiratory curve because the respiratory body movement is relatively small.

Figure 17:
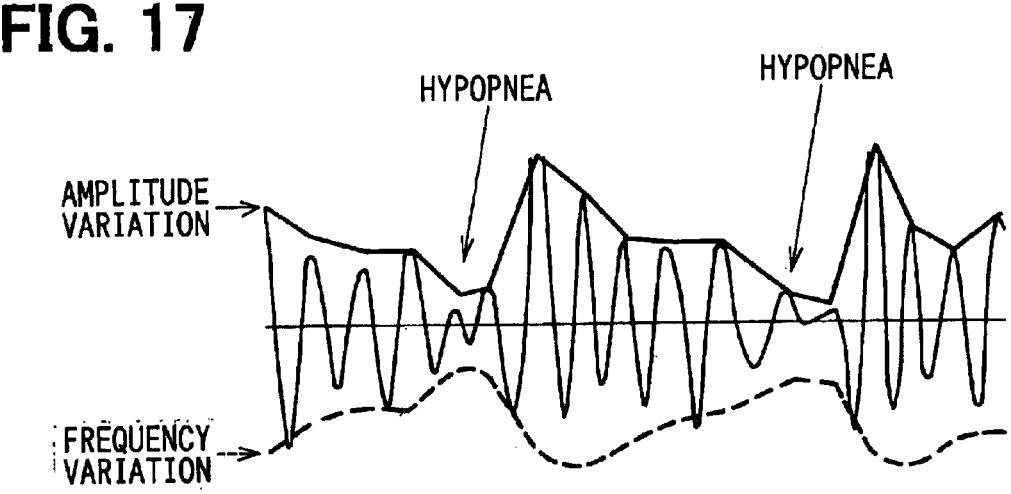
FIG. 17 is a waveform showing variations in amplitude and frequency.

The respiratory rate increases after the hypopnea with respect to the normal respiratory rate. Referring to FIG. 17, the amplitude and the frequency of the respiratory curve decrease during the hypopnea. They increase during the respiration recovery from the hypopnea. By detecting variation in frequency of the respiration curve in addition to the amplitude, the accuracy of the hypopnea detection improves.

Step S640 can be omitted from the process since the apnea/hypopnea can be detected in step S650. The apnea/hypopnea detection may be made based on only the frequency of the respiration curve.

The values used in steps S640 and S650 are not limited to 2.7 and 2.0, respectively. From experiments using values equal to or larger than 1.4, the results of the apnea/hypopnea detection are similar to results of the same performed by a definite diagnosis system. The definite diagnosis system detects apnea/hypopnea based on the oxygen saturation of blood, air flow in a mouth and nose, chest movements, and abdominal movements. The correlation between the results of those two systems is higher than 0.9. Therefore, values other than 2.7 or 2.0 can be used as long as they are equal to or larger than 1.4.

In the apnea/hypopnea analysis, the number of portions to obtain an average used as the maximum value is not limited to three. Two portions, four portions or more can be used. Alternatively, an amplitude of each portion can be used as the maximum value without averaging out several portions. However, noise components can be effectively reduced by using an average of several portions even when the amplitude of the respiratory signal increases due to periodic limb movements. A periodic limb movement causes noise in the respiratory signal and the noise increases the amplitude of the signal. The accuracy of the detection can be increased when the average of several portions are used. This is the same for the variation detection in frequency of the respiratory curve.

Figure 18:
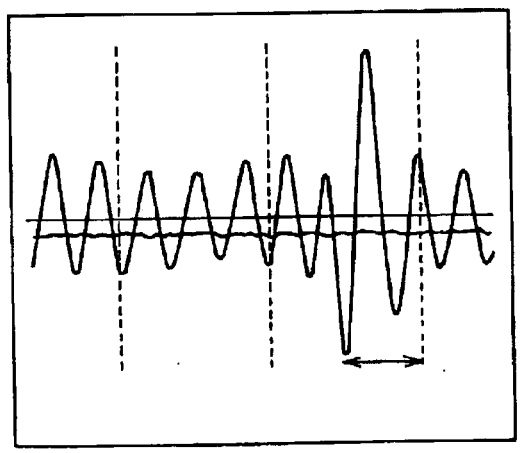
FIG. 18 is one example of a waveform, amplitude of which lowers faster than a predetermined period.

To improve the accuracy of the detection, the amplitude of the respiratory signal may be monitored for detecting variations at the maximum value as shown in FIG. 18. When the amplitude lowers faster than the predetermined period, it is determined the respiration recovering movements is caused by other factors. This is because deep rapid respirations normally continue for several times.

Furthermore, the amplitude of the respiratory signal may be monitored for detecting variations during a predetermined period before the minimum value. If the amplitude does not lower, the apnea/hypopnea should not be determined. This improves the accuracy of the detection.

Information other than the number of the apnea/hypopnea occurred in unit time can be displayed on the monitor 34. The information may include a period that body movements other than the respiratory movement occur, the number of respirations during sleep, and sleeping time. Alternatively, the number and the information can be stored in media or printed out.

Figure 20:
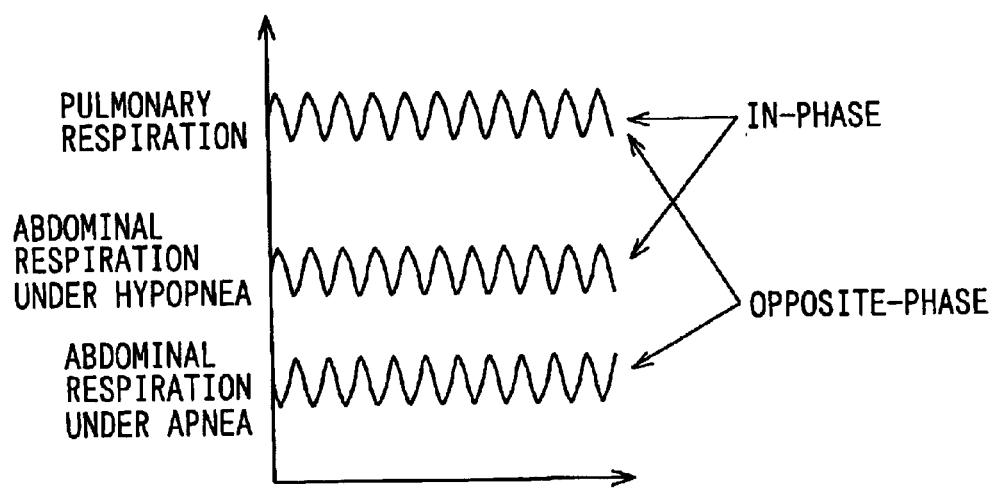
FIG. 20 is a chart showing phase relationships between waveforms under different conditions.

The signals from elements around a chest area and an abdominal area tend to be in opposite phase during the apnea and in phase during the hypopnea as shown in FIG. 20. Therefore, the distinction between the apnea and the hypopnea can be made based on the phase differences. The information can be stored or displayed for the apnea or the hypopnea.

The apnea/hypopnea can be determined by detecting a variation in frequency of the respiration curve from high to low. In this case, time that the person returns to normal respiration after the respiration recovery movements is detected.

The present invention should not be limited to the embodiment previously discussed and shown in the figures, but may be implemented in various ways without departing from the spirit of the invention. For example, the ten power spectrums may be selected before the calculations of the average $\alpha$ and the average $\beta$ (S42, S43). The elements may be selected based on the comparison between the average $\alpha$ and the average $\beta$, or the comparison between the average $\alpha$ and the average $\gamma$.

The specific values used in the embodiments may be altered according to characteristics of the system 1, such as characteristics of the pressure-sensitive elements 221 and a configuration of the sensor sheets 22. The respiration curve may be calculated based either in-phase signals or opposite-phase signals.

The weight sensors are not limited to pressure-sensitive elements 221. The number of the weight sensors is not limited to one hundred and sixty two. A window for displaying the information on the respiratory conditions may be provided on a conventional TV monitor. Other conventional display devices can be used for displaying the information. The respiratory signals may be stored in a memory device as a reference data for diagnoses. The data may be transmitted to hospitals via public networks.

What is claimed is:

1. A respiratory monitoring system, comprising:
   a plurality of sensors that produces weight signals corresponding to forces applied by a person under respiratory monitoring during sleep;
   a respiratory signal producing means that produces a respiratory signal representing respiratory conditions of the person based on the weight signals;
   a sensor selection control means that outputs switching signals;
   a sensor selecting means that selects sensors based on the switching signals;
   a signal converting means that converts weight signals outputted from the sensors that are selected by the sensor selecting means to digital signals;
   a signal strength determining means that determines a signal strength in a respiration frequency band corresponding to the respiratory body movement and a signal strength in another frequency band;
   a signal strength comparing means that compares the signal strength in the respiration frequency band with the signal strength in the other frequency band;

a signal selecting means that selects weight signals having a signal strength in the respiratory frequency band with a predetermined ratio to the signal strength in the other frequency band; and a target sensor selecting means that selects the sensors outputting the signal selected by the signal selecting means, wherein the respiratory signal producing means produces the respiratory signal based on the weight signals outputted from the sensors that are selected by the target sensor selecting means.

2. The respiratory monitoring system according to claim 1, wherein:

the signal strength determining means determines a signal strength in the respiration frequency band and a signal strength in a frequency band lower than the respiration frequency band; and the signal selecting means selects weight signals, the signal strengths of which have predetermined ratio to the signal strengths in the frequency band lower than the respiration frequency band.

3. The respiratory monitoring system according to claim 2, wherein the signal selecting means selects weight signals having en averages of the signal strengths in the respiration frequency band are predetermined times higher than averages of the signal strength in the frequency band lower than the respiration frequency band.

4. The respiratory monitoring system according to claim 1, further including a bias component removing means that removes a bias component from the weight signals prior to selecting the sensors by the target sensor selecting means, the bias component indicating a load applied to the sensor due to a weight of the person.

5. The respiratory monitoring system according to claim 1, further comprising a person presence determining means that determines presence of the person on top of the sensors.

6. The respiratory monitoring system according to claim 1, wherein:

the respiratory signal producing means determines whether an amplitude of the respiratory signal is smaller than a predetermined level for a predetermined period;

the target sensor selecting means reselects the sensors when the amplitude is smaller than the predetermined level for the predetermined period; and the respiratory signal producing means reproduces a respiratory signal based on weight signals outputted from the reselected sensors.

7. The respiratory monitoring system according to claim 1, wherein:

the signal strength determining means determines a signal strength in the respiration frequency band and a signal strength in a frequency band higher than the respiration frequency band; and the signal selecting means selects weight signals, the signal strengths of which have a predetermined ratio to the signal strengths in the frequency band higher than the respiration frequency band.

8. The respiratory monitoring system according to claim 7, wherein the signal selecting means selects weight signals having averages of the signal strengths in the respiration frequency band are predetermined times higher than averages of the signal strength in the frequency band higher than the respiration frequency band.

9. A respiratory monitoring system for a sleep apnea syndrome examination comprising:

a respiratory signal producing means that produces a respiratory signal representing a variation in weight applied due to a respiratory body movement of a person under the sleep apnea syndrome examination; and a determination means that detects apnea or hypopnea of the person based on a variation in frequency of the respiratory signal wherein:

the determination means monitors a variation in amplitude of the respiratory signal;

the determination means detects apnea or hypopnea when the amplitude of the respiratory signal decrease, increase, and then decrease with time and a frequency of the respiratory signal increases as the amplitude of the same increases.

10. The respiratory monitoring system according to claim 9, wherein:

the determination means calculates an amplitude average from a plurality of respiratory signals;

the determination means detects the variation in amplitude based on the calculation.

11. The respiratory monitoring system according to claim 9, wherein the determination means determines that the amplitude of the respiratory signal varies from a decreasing state to an increasing state when a variation rate of the respiratory signal is equal to or more than 1.4.

12. The respiratory monitoring system according to claim 9, wherein the determination means determines that a respiratory condition of the person is normal when a condition that the amplitude increases and the frequency is high continues less than a predetermined period.

13. The respiratory monitoring system according to claim 9, further comprising a distinguishing means that distinguishes between the apnea and the hypopnea based on a phase difference in weight signals according to a respiratory body movement in a chest area and an abdominal area.

14. The respiratory monitoring system according to claim 13, wherein the distinguishing means determines the hypopnea when the weight signals are substantially in phase and the apnea when the weight signals are substantially in opposite phase.

15. The respiratory monitoring system according to claim 9, further comprising a sleeping posture determination means that determines a sleeping posture of the person during sleep based on a variation in a number of the sensors detecting a weight.

16. The respiratory monitoring system according to claim 15, wherein the calculation means calculates the number of times that the apnea or the hypopnea is detected for each sleeping posture determined by the sleeping posture determination means.

17. The respiratory monitoring system according to claim 9, wherein the respiratory signal producing means stops producing the respiratory signals while the weight distribution is changing.

18. The respiratory monitoring system according to claim 9, wherein the person presence detecting means detects the absence of the person when the variation in weight due to the respiratory body movement is absent.

19. The respiratory monitoring system according to claim 18, further comprising a person presence detecting means that detects a presence or an absence of the person based on a weight applied by an object on the sensors, wherein the respiratory signal producing means stops producing the respiratory signals when the person presence detecting means detects the absence of the person.

20. A respiratory monitoring system for a sleep apnea syndrome examination comprising:

a respiratory signal producing means that produces a respiratory signal representing a variation in weight applied due to a respiratory body movement of a person under the sleep apnea syndrome examination; and wherein the determination means detects apnea or hypopnea when the frequency of the respiratory signal varies from low to high when a period of the respiratory signal becomes 0.5 second shorter than the previous signal.

21. The respiratory monitoring system according to claim 20, wherein the respiratory signal producing means stops producing the respiratory signals while the weight distribution is changing.

* * * * *